United States Patent [19]

Muir

[11] Patent Number: 4,759,356

[45] Date of Patent: Jul. 26, 1988

[54] TRACHEOSTOMY DEVICE AND RELATED METHODS

[76] Inventor: David Muir, Passy & Passy, Inc., 4521 Campus Dr., Irvine, Calif. 92715

[21] Appl. No.: 936,144

[22] Filed: Oct. 3, 1986

Related U.S. Application Data

[63] Continuation-in-part of Ser. No. 709,543, Mar. 8, 1985, abandoned.

[51] Int. Cl.⁴ ............................................. A61M 16/00
[52] U.S. Cl. ............................... 128/207.16; 128/912; 623/9
[58] Field of Search .................. 128/207.16, 207.15, 128/207.14, 200.26, 207.17, 912; 623/9

[56] References Cited

U.S. PATENT DOCUMENTS

| | | | |
|---|---|---|---|
| 3,137,299 | 6/1964 | Tabor | 128/207.16 |
| 3,693,624 | 9/1972 | Shiley et al. | 128/207.15 |
| 3,844,296 | 10/1974 | Birch et al. | 128/207.16 |
| 4,029,105 | 6/1977 | Faust | 128/207.17 |
| 4,040,428 | 8/1977 | Clifford | 128/207.16 |
| 4,325,366 | 4/1982 | Tabor | 128/207.16 |
| 4,416,273 | 11/1983 | Grimes | 128/912 |
| 4,501,933 | 4/1985 | Wendt et al. | 128/912 |
| 4,506,665 | 3/1985 | Andrews et al. | 128/912 |

Primary Examiner—Edward M. Coven
Assistant Examiner—K. M. Reichie

[57] ABSTRACT

Methods for improving speech and other functions of a tracheostomized patient are disclosed, together with an apparatus for carrying out the methods. The methods involve providing the patient with a tracheostomy valve that prevents airflow at all times except when the patient inhales. A way for doing so by positively biasing a flexible diaphragm against a valve seat is disclosed, together with a rivet structure for effecting such bias.

24 Claims, 2 Drawing Sheets

TRACHEOSTOMY DEVICE AND RELATED METHODS

This is a continuation-in-part based on the inventor's copending patent application Ser. No. 709,543, filed Mar. 8, 1985, now abandoned, the date of which is claimed with respect to the common subject matter of the applications.

BACKGROUND

This invention relates to tracheostomy valves, for use on tracheostomy tubes; it also relates to methods of restoring and improving the physiological function of patients who have tracheostomy tubes. The general background of the invention is described in Birch U.S. Pat. No. 3,844,290 and Tabor U.S. Pat. Nos. 3,137,299 and 4,325,366, which also exemplify the prior art. The prior art describes valves that tend to block passage of air outward through the tracheostomy tube during exhalation, but permit passage of air inward to the lungs through the tracheostomy tube during inhalation.

It has been discovered that a number of undesirable effects result from less than total blockage of airflow through a tracheostomy valve during all or part of the exhalation phase of the respiration cycle. Partial airflow through the valve during the exhalation phase is required by such inventions as that of Tabor U.S. Pat. No. 4,325,366, and is likely to occur with devices such as that of Birch U.S. Pat. No. 3,844,290. The passage of moisture-laden breath through the tracheostomy tube to the ambient atmosphere tends to produce deposits of moisture and mucus on the walls of the valve housing. Such deposits tend to increase friction, making the valve more difficult to open during inhalation. They may also act as a culture medium for pathogens, such as pseudamonas bacteria. Further, such valves tend to click and produce vibration in use, particularly at the beginning of the exhalation cycle, which disturbs the patient. Finally, the speech of users of such valves is not normal and is frequently unintelligible.

It is noted that some prior art devices, such as that of Tabor U.S. Pat. No. 3,137,299, may be considered to suggest providing a one-way tracheostomy valve that entirely blocks airflow during the exhalation phase, but they do not expressly teach that it is important or beneficial to do so. Moreover, other prior art devices, such as that of Tabor U.S. Pat. No. 4,325,366, expressly teach in the opposite direction, i.e., to leave a certain amount of valve opening so as to permit airflow at the beginning and end of the exhalation cycle. It is believed that no prior art device teaches that beneficial results occur in tracheostomized patients as a result of totally blocking airflow through the tracheostomy valve except during inhalation, and that no teaching exists of any structure expressly devised to insure such blockage.

It has been observed clinically that tracheostomized patients frequently have one or more of the following problems, adversely affecting their normal physiological function, and resulting from the tracheostomy:

(1) Loss of speech. This results from the diversion of air through the tracheostomy tube, bypassing the larynx and oral and nasal cavity.

(2) Loss of olfactory sensation. It is believed that this results from the same diversion of air. Loss of olfaction has an adverse effect on appetite, and may lead to loss of weight.

(3) Increased nasal and oral secretions. This results from the diversion of air away from the oral cavity and also from the diversion of air from the nasal cavity. The diverted air would otherwise have facilitated the evaporation of these secretions.

(4) Decreased oxygenation of blood. It is believed that this results from decreased pressure created in the alveoli of the lung, as a result of an open exit path (or lower resistance path) for air via the tracheostomy tube.

(5) Increased infections of respiratory tract. It is believed that this results from several causes. One is that finger occulusion of the neck is a common practice among tracheostomized patients; this practice occurs because patients are dissatisfied with, and therefore do not use, existing tracheostomy valves. Finger occulusion promotes infection, because of contaminating material that may be on the fingers. A second factor is lack of filtration of inhaled air, since it does not traverse the nasal cavity. It is believed that these factors promote pneumonitis. It is believed that another factor causing increased infection is the accumulation of moisture and mucus in existing tracheostomy devices, which provides a culture medium for pathogens. Increased oral and nasal secretions, noted above, may be a further causative factor of the same type.

(6) Difficulty in swallowing. This is associated with aspiration of food and fluids, and may lead to pneumonia or upper respiratory infections. Although it is not believed that the literature has associated this with particular characteristics of tracheostomy devices, the inventor believes that this results, as described below, from an imbalance of pressure within the throat, as a result of tracheostomization.

(7) Abnormal expectoration. It has been observed that tracheostomized patients expectorate into and through their tracheostomy tubes. When a person coughs, mucus, fluid, or other matter is expelled upward from the lungs to the trachea. In a normal person, this matter passes upward through the trachea past the epiglottis into the mouth, and is then expelled. In a tracheostomized patient, however, there is a low resistance parallel path through the tracheostomy tube. This permits matter to be driven from the lungs into the tube and at times to be ejected from the tube.

(8) Difficulty in decannulation. Decannulation is the removal of a tracheostomy tube, once the medial need for its presence had ended. It has been observed clinically that it is often difficult to decannulate patients, particularly pediatric patients, because the patients are afraid that they cannot breath without the tube. This makes it difficult to rehabilitate such patients.

These effects have not been correlated with particular characteristics or structures of tracheostomy tubes or related apparatus.

SUMMARY OF INVENTION

It was discovered that the problems described above may be lessened or overcome by providing a tracheostomy valve with a firm, positive closure, so that the valve is closed at all times except during inhalation. This result is accomplished by providing a slight bias on the valve, so that a pressure differential of approximately 8 to 15 mm of water head is required to move the valve diaphragm off the valve seat. The valve is thus closed entirely during the exhalation phase of the respiration cycle and also at the very beginning and end of the inhalation phase of the cycle. It is believed that this mode of operation is essential to the elimination of various physiological functions associated with tracheostomization. A preferred embodiment of the invention accomplishes this by preloading an elastic diaphragm against a valve seat, by means of compressing a rivet to a predetermined length.

This modification of the structure of a tracheostomy valve has been found to make much more intelligible in tracheostomized patients, so that persons who could not communicate orally in the past have been made able to carry on normal or improved speech. At the same time, there has been a concimitant elimination of valvular noise and vibration, and also elimination of accumulation of secretions in the valve unit.

In addition, it has been discovered that a number of surprising and unexpected additional beneficial effects have occurred as a result of the use of this type of valve. These include: clearer and stronger speech, greatly improved ventilation of the lower respiratory tract, improvement of olfactory sensation and consequent improvement of appetite, improved swallowing, decreased aspiration of food and fluid, improved oxygenation of pulmonary blood, and lessened upper respiratory infection. It has also been observed that the use of the valve of this invention facilitates decannulation of tracheostomy patients and their rehabilitation to normal breathing.

DETAILED DESCRIPTION OF INVENTION

Figure 1:
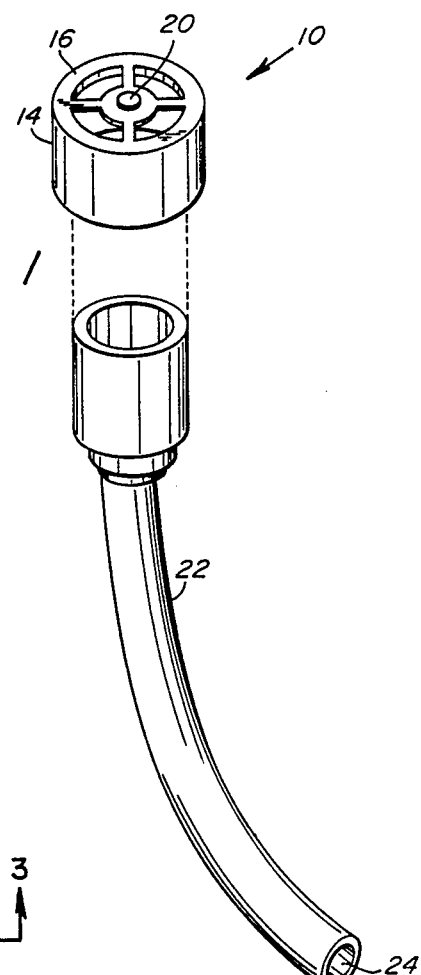
FIG. 1 is an exploded isometric view of a tracheostomy valve assembly and associated tracheostomy tube assembly.

It has been discovered that preventing any airflow through a tracheostomy valve during the exhalation cycle results in a number of beneficial results for tracheostomy patients. Although the initial purpose and motivation behind the invention was to faciliate speech by means of an automatic tracheostomy device that would permit recovery of the power of intelligible speech, it was discovered that the device of this invention provided significant other physilogical benefits as well. It is believed that these benefits have not hitherto been discovered because workers in the field have lacked a motivation that would point them in the direction of these discoveries. A brief narrative account of how the the invention occurred will facilitate understanding the structure of the device, the results it provides, and the relationship of results to structure.

A tracheostomized patient ordinarily speaks by placing a finger against his or her neck to block the tracheostomy opening (stoma), thereby redirecting air through the larynx, and then the mouth and nose. However, if the patient is unable to do this because he cannot appropriately move his arms; he cannot speak unless either someone else places his or her finger against his stoma or he is otherwise provided with an automatic closure mechanism. However, prior to the development of the instant invention, an automatic tracheostomy valve was not available on the market.

The initial product was somewhat like the hypothetical device described in the Tabor U.S. Pat. No. 3,137,299 patent. (No such device is available on the market.) But the initial device did not provide intelligible, natural sounding speech. Instead, it produced whistles, clicks, and gurgling sounds in operation, particularly when exhalation pressure pulses struck the diaphragm. This not only interferes with the intelligibility of speech but it disturbs, embarrasses, and depresses the user, and intereferes with the user's attempts at self-rehabilitation. After considerable experimentation, it was concluded that the lack of positive closure of the diaphragm at the beginning of the exhalation pulse was the cause of the problem, and that providing such closure alleviated it. That made it possible to devise an automatic tracheostomy valve that restored the power of intelligible speech to tracheostomized patients.

However, a number of other elements must be combined to provide the desired effect. First, a very soft, flexible diaphragm for the valve is essential. It has been found that certain silastic material has appropriate properties for this purpose. To provide the right resiliency, the ratio of diameter and thickness, and also the relative sizes of the diameter and supporting rivet, are important. These points are described in more detail below.

It is important to provide a slight positive bias of the diaphragm against the valve seat, to insure that airflow is entirely blocked except during inhalation. However, too much bias makes it difficult for the patient to breath or may cause a discontinuity in airflow during inhalation, which may cause vibration and/or noise and is disturbing. As described more fully below, it has been found that a bias (pressure) of approximately 8 to 15 mm of water head provides an optimal bias and resistance to airflow.

As a result of these efforts, a new, improved speaking-valve means for facilitating speech and improving the strength and clarity of speech has been provided. The automatic valve described above has permitted a patient to recover the power of intelligible speech. Then, a number of unexpected benefits that resulted from the use of this device were discovered. Although these results were not anticipated before the new valve was developed, it is now possible with hindsight to recognize that they resulted from the structure of the improved speaking valve of this invention, and to explain how the results occurred.

It is considered that the present invention therefore includes both the new mechanical structure that was invented to provide the improved tracheostomy valve described below, and also the new methods of bringing about various physilogical benefits that were discovered in the course of testing and improving the new device. The methods, which are believed hitherto unknown, include alleviation of a number of dysfunctions caused by tracheostomization and the improvement of a number of physiological functions; often, the dysfunction and function are a pair of correlatives, but in some instances ordinary usage includes only one or the other of the two.

First, the physilogical methods that were discovered will be described and then the mechanical structure that was devised to accomplish those results. The methods are described in an order not necessarily that of their importance or value, which requires a hindsight evaluation of the discoveries, but rather in terms of how they come to be discovered. It will be noted that some benefits result directly from and are caused by the improved structure of the new valve, which entirely blocks all airflow except during inhalation. Other benefits result indirectly from the structure. That is, they result from use of a valve, as contrasted with an unvalved tracheostomy tube, and the benefits may be realized to some extent with a valve that is not biased to have a positive closure. But these benefits are considered to be indirectly caused by the improved structure, in that without the improvements and direct benefits of the new valve the patient has no motivation to use a valve at all, since prior valves were not effective in improving speech or otherwise motivating patients to use them. In contrast, the new valve creates a motivation to utilize a valve, which in turn leads to realization of the indirect benefits along with the direct benefits.

Methods

Improvement of speech

As indicated above, the original purpose of this invention was to restore the power of speech to persons deprived of that power by tracheostomization. The invention has restored the power of speech to many persons who were unable to speak intelligibly by use of other means. It also provides clearer, stronger, more intelligible speech to tracheostomized patients who were previously able to speak to some extent by use of other means (such as finger occlusion of the stoma).

Improvement of olfaction

As indicated earlier, in the Background section of this specification, olfactory sensation typically disappears in tracheostomized patients, because their upper respiratory tracts (sinuses) lack regular airflow. It is known that loss of olefaction results in loss of appetite. After using this invention it was noticed that olfactory power was returning, and this was associated with improved appetite. It was found that other users of the invention reported the same result.

It is believed that this may be attributed to the regular redirection of airflow through the upper airway, nose, and mouth, which is caused by the automatic valve action of the invention. It is known that sensory cells for olfaction are located in this part of the body. This and further observations were brought to the attention of medical specialists in this field, who confirmed them by clinical observations with their patients and in some instances by appropriate tests.

Decreasing of nasal and oral secretions

It was also noticed that there was a marked decrease in secretions of oral and nasal chambers. This decrease is attributable to evaporation of such secretions by the automatic and continual redirection of air through these chambers by the invention. It is believed that the invention thus restores a normal physiological function (evaporation of secretions) that was impaired by tracheostomization.

Improvement of oxygenation

A sense of increased well being was also experienced, which is attributable to improved oxygenation caused by the use of the invention. Because the new valve is closed at all times except during inhalation, increased back pressure occurs in the lungs and ultimately the alveoli. It is believed that increased pulmonmary back pressure increases gas exchange and oxygen uptake in the alveoli. Studies and experiments to confirm these observations are now in progress at the University of California-Irvine.

Lesseing of chronic infections

A lower frequency of infections, a chronic problem of tracheostomy patients was experienced. Both stomal and pulmonary infections are associated with tracheostomization. As indicated in the Background section of this specification, one causal factor is contaminants on fingers used to occlude an unvalved tracheostomy tube. Since the automatic valve of this invention eliminates finger occulsion, this vector of infection is eliminated.

In addition, the increased back pressure from the valve of this invention provides better ventilation of both the lower respiratory tract (e.g., lungs), and the upper respiratory tract (e.g., sinuses). To the extent that this promotes evaporation of secretions and lessens their accumulations in the respiratory tract, culture media for bacteria are eliminated. Furthermore, the invention provides a generally drier tracheostomy tube and valve, so that they too are less likely to harbor and breed pathogens, which further tends to lessen the likelihood of infections.

It has been observed that the valve must be washed frequently to remove accumulations of dust and dirt. This matter is contained in the ambient air. While a normal person is able to filter much of this matter out of inhaled air by means of his or her nasal chambers, tracheostomization bypasses these natural filters. However, the structure of the valve of this invention causes it to act as a filter, as is evident from the above-described dust and dirt accumulation. Thus, the invention helps reduce pneumonias and other pulmonary infections by filtering sources of infection from the inhaled air.

Finally, it may be noted that the presence of the valve helps prevent pediatric patients from putting small objects down their tracheostomy tubes. Among other things, this lessens opportunity for resulting infections.

Improved swallowing

The device improves swallowing. The swallowing mechanism involves a closure of the epiglottis which is preceded by compression (a muscle contriction wave) that moves down the throat pushing a bolus of food or other matter toward the stomach, against the resistance of the air compressed in the lower respiratory tract as this occurs. In a tracheostomized patient, the tracheal opening to the atmosphere interferes with the development of the pressure wave, in that it bleeds pressure off to the atmosphere. In a valve without positive closure, this effect also can occur.

However, the valve of this invention prevents that effect from occurring. Once the epiglottis closes off the trachea at the top and the compression wave begins descending the throat, there is no longer any exit path from the trachea because the valve of this invention closes off the only other exit. Users of this device have indicated that they experience improved swallowing and less aspiration of food or fluids. It is believed that this result is caused by the mechanical structure of the new valve.

Several other beneficial effects follow from the improvement in swallowing. First, eating is easier and more normal and comfortable. Second, there is less aspiration of food and water, or mucus, because when the swallowing reflex occurs the process works properly instead of being impaired by the exit of pressure via the tracheostomy opening. Hence, food and water are swallowed down the esophagus rather than aspirated into the trachea. Such aspiration is a potential cause of pneumonia, and elimination of aspiration is believed to lower the probability of penumonia in a tracheostomized patient.

Normalization of expectoration

The new valve provides more normal expectoration, so that the patient does not expel mucus and othe matter through the tracheostomy tube. If there is no valve, or if the valve is not firmly closed at all times except during inhalation, expectorated matter is forced into the tracheostomy tube and may be ejected out of the tube into the surroundings. However, the valve of this invention does not permit this to occur. The cushion of air in the closed tracheostomy tube prevents expectorated sputum or other matter from entering the tube, so that the matter flows past the tube and up the trachea for normal expectoration. This has been observed markedly to improve both the normal physiology and the normal hygiene of the patient, as well as eliminate possibly unpleasing experiences for persons in the vicinity of the patient.

Improvement in decannulation

As indicated earlier, decannulation sometimes creates fear and patients therefore object to decannulation. The use of the invention has been found to facilitate decannulation, because it reaccustoms the patient to airflow through the upper respiratory tract without interfering with inhalation via the tracheostomy tube. This facilitates rehabilitation of patients, because reaccustoming them to airflow through the upper respiratory tract helps assure them that decannulation and normal respiration is possible, and that they will not suffocate if the tube is removed.

Improvement of speech with in-line respirators

Although one-way valves exist for use with in-line respirators, those hitherto available have not been useful for speech. They have tended to clog and stick because of the accumulation of moisture and other matter, and have excessive drag and resistance. It has been found that the present invention can be used successfully in in-line respirators, where it permits patients to speak although that was not previously possible.

Apparatus

Having described the beneficial results of the invention and what is believed to be the rationales explaining them, a more detailed discussion of the structure of the apparatus that was devised to accomplish these results will be described. The following description is based on the preferred embodiment of the invention, which is the same as the present commercial device.

Figure 5:
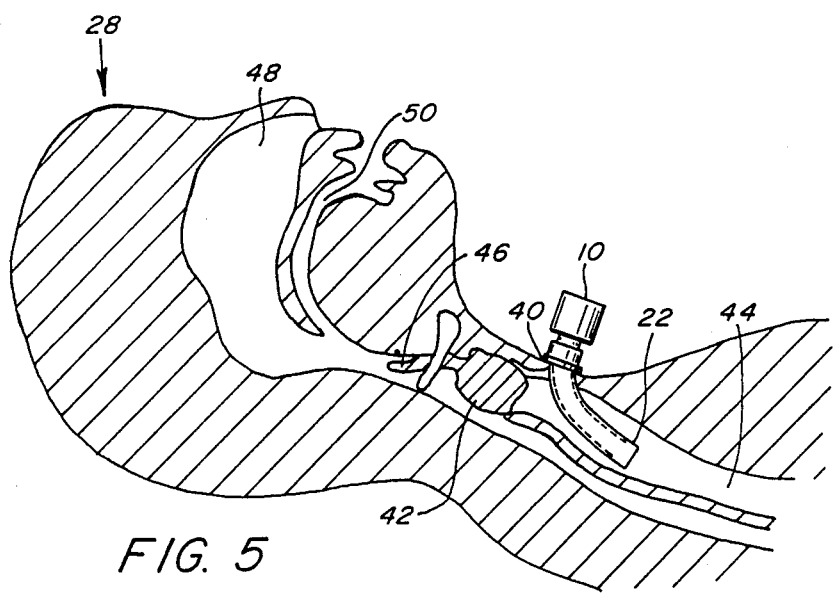
FIG. 5 is a sectional view of a patient with a tracheostomy tube to which the valve of the invention is attached.

FIGS. 1 and 5 illustrate the entire tracheostomy device system. FIG. 1 illustrates the improved tracheostomy valve unit 10 of the invention, shown in association with a tracheostomy tube assembly 22. FIG. 5 illustrates how the entire system is located with respect to a patient's trachea.

Figure 3:
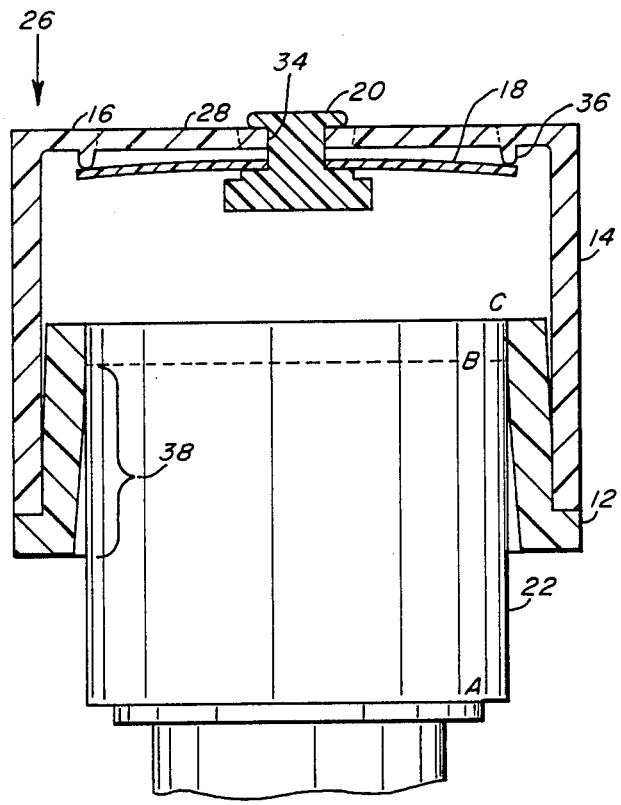
FIG. 3 is a sectional view of the valve assembly. The section is along the line 3—3 of FIG. 2.

The preferred embodiment of this invention is a valve assembly unit 10 having five principal parts: connector 12, valve base 14, support 16, diaphragm 18, and rivet 20. FIG. 3 is a cross sectional view of the valve assembly, showing these parts. FIG. 1 is an isometric view showing these parts, except for diaphragm 18.

As shown in FIG. 1, tube assembly 22 has a tracheal end 24. As shown in FIG. 5, the latter end of tube assembly 22 is inserted into the trachea 44 of patient 28. The other end of tube assembly 22 is removably fitted into and frictionally engages with connector 12 of valve assembly 10, as shown in FIG. 3. Connector 12 is made of high impact plastic material, and is shown in section in FIG. 3. Connector 12 has an O.D. of approximately 0.8 inches.

Connector 12 is fitted into a tubular valve base 14, as shown in FIG. 3. Valve base 14 is made of the same plastic material and the two parts are manually press fitted and bonded with a solvent such as methyl ethyl ketone. The O.D. of valve base 14 is approximately 0.9 inches, and its I.D. is approximately 0.8 inches. It is approximately 0.65 inches high. Connector 12 preferably has a slight external taper to facilitate pressing it into valve base 14. (It also has an internal taper, discussed below, to facilitate its receiving tracheostomy tube 22.)

Figure 2:
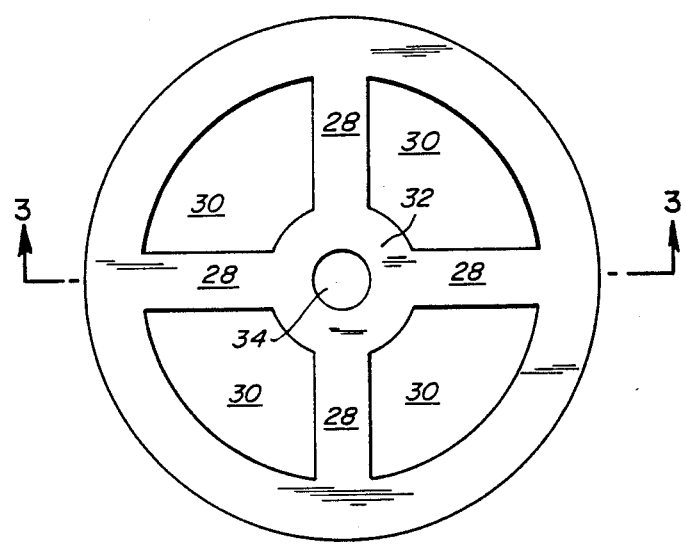
FIG. 2 is a plan view of the valve assembly from the vantage point of viewing the valve unit from the side toward the ambient air (i.e., external to the patient using the device).

FIG. 2 shows a plan view of valve base 14 viewing it from its external end 26, i.e., the end of the valve assembly that is opposite to tracheostomy tube 22. (External end 26 is also hereinafter referred to at times as the proximal end of the valve assembly.) This is the viewpoint taken along the arrow associated with the number 26 in FIGS. 3 and 4. External end 26 of valve base 14 includes support 16, which is a ring-shaped member with a four-armed cross-piece 28 dividing the interior of external end 26 into four air ports 30. Cross-piece 28 has a disk-shaped member 32 at the center, through which an axial hole 34 passes; rivet 20 passes through hole 34. Support 16 is in effect a transverse wall of the valve base housing, extending radially inward from the inner walls thereof. In the preferred embodiment of the invention, valve base 14 is molded to include support 16 and cross-piece 28, as well as disk 32, as a single integral unit.

Figure 4:
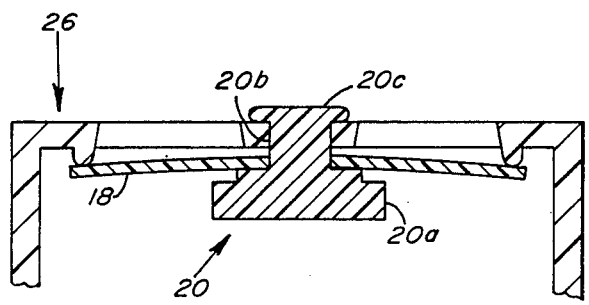
FIG. 4 is a detailed sectional view (along a different sectional line) of the portion of FIG. 3 where the bias-controlling rivet through the diaphragm is located. This figure shows the bias and curvature of the valve diaphragm in an exaggerated manner to facilitate appreciation of that feature.

As seen more advantageously in FIGS. 3 and 4, support 16 has a seating ring 36 around the outer periphery of its air ports 30, and diaphragm 18 is pressed by rivet 20 against seating ring 36 to provide a positive closure contact.

Diaphragm 18 is mounted to support 16 by rivet 20. The diaphragm is silastic material, approximately 0.015 thick which is approximately 1/50 the O.D. of the diaphragm, and it has an axial hole through which to pass rivet 20. The diaphragm is a transparent, low modulus silicone sheet, Dow Corning Silastic, medical grade.

Rivet 20 is made of the same material as the valve base and connector. It is illustrated in greater detail in FIG. 4, and it is shown compressed into its final configuration. Rivet 20 has a head 20a and a shank 20b approximately 0.12 inches in length when initially inserted through the axial hole of the diaphragm and axial hole 34 of supporting disk-shaped member 32, and before compression. After compression, part of shank 20b has "mushroomed" into staked end 20c. (Head 20a is not changed.)

As described earlier, the invention requires that diaphragm 18 be biased closed. This is accomplished as follows: As shown in FIGS. 3 and 4, support 16 has a raised valve seating ring 36 on its inner face. The diaphragm is initially fastened to the cross-piece with an axial, longitudinally disposed, "floating rivet." This permits the diaphragm initially to "float" longitudinally on the rivet, i.e., axially within valve base 14. Then the rivet is compessed to bias the diaphragm against the valve seat, which is slightly raised toward the diaphragm with respect to the inner surface of cross-piece 28. The more the rivet is compressed, the more firmly the diaphragm is pulled up against the valve seat. This in turn biases the diaphragm more strongly against leakage airflow at the beginning of exhalation.

In the preferred embodiment, valve seating ring 36 is raised approximately 0.015 inches from the inner face of support 16. (As shown in FIGS. 3 and 4, the bottom of valve seating ring 36 extends below the bottom surface of the rest of support 16, such as the bottom of cross-piece 28, by a distance which is here specified as approximately 0.015 inches.) Thus, if rivet 20 is given 0.007 inches of end play after compression, it preloads diaphragm 18 approximately 0.008 inches toward seat 36. (As shown in FIG. 3, if the air gap between the top of diaphragm 18 and the bottom of cross-piece 28 of support 16 is 0.007 inches, then 0.008 inches of the thickness of diaphragm 18 [which is 0.015 total inches thick] will have to be moved up above the bottom of valve seating ring 36 and into the space enclosed within the valve seating ring. That occurs because the distance between the bottom of cross-piece 28 and the bottom of valve seating ring 36 is 0.015 inches). That is, considering the "central portion" of diaphragm 18 to be that portion thereof immediately surrounding rivet 20, as shown in FIG. 4, the upper part of the central portion of diaphragm 18 is pressed into the lower part of the space surrounded by the bottom of valve seating ring 36. Approximately half of the thickness of diaphragm 18 is above an imaginary plane laterally extending across the very bottom of valve seating ring 36, and approximately half of said thickness is therebelow. As shown in FIG. 4, however, the amount of extension of diaphragm 18 into said space is slightly exaggerated, in order to make it easier to visualize the structure. (In FIG. 4, nearly all of the very central portion of diaphragm 18 is shown as pressed into said space, rather than just half).

It has been found that this amount of preloading results in a bias equivalent to approximately 8 to 15 mm of water head, with the 0.015 silastic diaphragm described above. It also results in making diaphragm 18 seat completely against seat 36. It will be noted, also, that approximately half of the thickness of the diaphragm is pressed, at the central portion of the diaphragm, beyond the plane of the bottom of the valve seat when this amount of preloading is used. That is, approximately half the thickness of the central portion of the diaphragm is displaced within the valve seating ring. This has been found to produce an effective closure that maintains a positive, uninterrupted contact all along the seating ring.

The effective length of rivet 20 is established during installation by blocking head 20a of the rivet with an adjustable support while at the same time heat-staking end 20c. Adjustment of the adjustable support then compresses rivet 20 and forms heat-staked end 20c, which mounts the diaphragm to support 16 and preloads diaphragm 18. A staking machine may be designed for this purpose using conventional technology; the heat should be selected to 350° F. to within 10°.

Returning to FIG. 3, it is seen that connector 12 has a coupling section 38 for frictionally engaging tracheostomy tube 22. In the preferred embodiment, section 38 is tapered so that it can be placed onto all tracheostomy tubes with standard 15 mm hubs and of diameters ranging from 14.9 to 15.4 mm. This is accomplished by having an entrance tapered from an initial I.D. of 15.5 mm at point A until the taper intersects a cylindrical bore of approximately 15.3 mm at point B, and then the cylindrical bore continues until point C. This permits enough room for compression of the tracheostomy tube and expansion of the housing to provide a snug frictional fit for the various I.D. tracheostomy tubes indicated, where all of the different tubes extend approximately the same amount into the housing and are firmly connected to it without interfering with the valve closure at the externally directed end.

This feature permits universal fit of the improved valve assembly onto all standard tracheostomy tubes in current use, so that the invention is not restricted to use with any particular type of tracheostomy tube. The invention has also been found useful with in-line respirators. It is believed that until this invention it was not feasible to use tracheostomy tube valves on respirators, in a way that provided intelligible speech.

FIG. 5 shows a patient 28. Patient 28 has a tracheostomy neck opening 40 which is below the patient's larynx 42 and extends to the patient's trachea 44. Tracheostomy tube 22 is inserted through neck opening 40 and is retained in any suitable manner. As described above, the tracheostomy valve assembly 10 is removably mounted on tube assembly 22. When the patient inhales, the system permits airflow into trachea 44. When the patient exhales, the valve totally blocks airflow from trachea 44 through the valve to the atmosphere; at the same time, the valve redirects airflow upward in the direction of larynx 42 and epiglottis 46, toward sinuses 48 and mouth 50.

Although the invention has described a preferred embodiment and exemplified it in terms of the actual commercial device, it will be understood that the scope of the invention is not limited to that description. Changes and modifications will occur to those of ordinary skill in this art and they can be made without departing from the spirit and scope of the invention. In particular, it will occur to persons skilled in the art that other means may be provided for totally preventing escape of air from the trachea during exhalation while permitting ingress of air for inhalation, whereby the desirable physiological effects of the invention will be accomplished. The invention is considered to include the method of accomplishing those results as well as structures designed to accomplish them, when the means of accomplishment is substantially complete prevention of escape of all air during exhalation.

As used in the claims, "firmly seated against and making a positive closure contact with" or like words refer to a positively biased contact, such as that caused by the rivet's preloading the diaphragm to bias it against the valve seat, as described above.

As used in the claims, "biased against said valve seating means by a rivet which is longitudinally compressed to a predetermined length" or like words refer to having a valve seat raised slightly away from a support member to which is mounted a diaphragm on a rivet, so that when the rivet is compressed to a particular length, the diaphragm cannot float freely in a longitudinal direction. Instead, the center of the surface of the diaphragm facing the valve seating ring is placed between the tracheal plane of the valve seat and the tracheal plane of the support, thereby preloading the diaphragm in a manner similar to that described above.

When reference is made to displacing the diaphragm's central portion within the valve seating means by a particular distance, or reference is made to the plane of the valve seat, it should be understood that the valve seating ring and the diaphragm are actually three-dimensional elements rather than two-dimensional planes, so that the relevant planes in question are those of (1) that surface of the diaphragm facing the valve seating ring and (2) that surface of the valve seating ring that faces the diaphragm, i.e., the tracheal surface of the ring.

When reference is made to the diaphragm's "rest" position, that means the position of the diaphragm when there is neither inhalation nor exhalation, so that the only pressure gradient on the diaphragm is that caused by compressing the rivet to preload the diaphragm.

The subject matter claimed is as follows:

1. A method of alleviating physiological dysfunction and improving bodily function in a patient who has been subjected to tracheostomization, where the dysfunction results from the tracheostomization and the function is impaired by the tracheostomization, the patient having a neck-opening into the patient's trachea, the neck opening being adapted to admit air into the trachea, said method comprising the steps of:
(1) providing a tracheostomy tube having
    a tracheal end adpated to be received in the patient's trachea,
    a proximal end adapted to be external to the patient's body and
    a tube passage extending therethrough, said tube passage having a tube inlet at said proximal end and a tube outlet at said tracheal end in the patient's trachea;
(2) inserting into the trachea via the neck opening said tracheostomy tube such that the tracheal end is received in the patient's trachea and the proximal end is external to the patient's body, whereby said tube conducts air to the patient's trachea from said inlet to said outlet via said tube passage;
(3) providing a tracheostomy valve unit adapted to cooperate with said tracheostomy tube inserted into the patient's trachea, having
    a first end adapted for connection to the proximal end of said tracheostomy tube,
    a second end,
    a valve's unit inlet located at the second end of said valve unit,
    conducting means for permitting airflow therethrough from said inlet through said valve unit and then to the tube to the patient's trachea when the patient inhales, and
    blocking means making positive, uninterrupted closure contact with the valve unit inlet and thereby, entirely blocking airflow through said conducting means from the tube and through said valve inlet at all times when the patient exhales and at all other times except when the patient inhales; and
(4) fluidically connecting said valve first end to said proximal end of said tracheostomy tube and thereby, permitting airflow from said valve unit inlet through said valve unit and then through said tube inlet to the patient's trachea when the patient inhales and entirely blocking airflow through said conducting means from said tube inlet and through said valve unit inlet to the ambient air at all times when the patient exhales and at all other times except when the patient inhales.

2. The method of claim 1 wherein the step of providing a valve unit further includes providing a valve unit having valve-seating means located between said valve unit inlet and said blocking means and blocking means comprising a thin flexible diaphragm means firmly seated against and making a positive, uninterrupted closure contact with said valve-seating means in said valve unit.

3. The method of claim 2 wherein said dysfunction that is alleviated is inability to speak intelligibly or the function that is improved is speaking.

4. The method of claim 3 wherein the following additional step is performed: providing a respirator having an air outlet means for delivering air to patients in the vicinity of the patient, and fluidically connecting said valve unit inlet to the air outlet means instead of directly to the ambient air.

5. The method of claim 2 wherein said dysfunction that is alleviated is increased accumulation of secretions in the patient's respiratory tract.

6. The method of claim 2 wherein said dysfunction that is alleviated is inability to swallow normally and the function that is improved is swallowing.

7. The method of claim 2 wherein said dysfunction that is alleviated is loss of olfactory sensation and the function that is improved is olfaction.

8. The method of claim 2 wherein said dysfunction that is alleviated is aspiration of food, body secretions, or other fluid.

9. The method of claim 2 wherein said dysfunction that is alleviated is expectoration into the tracheostomy tube and said function that is improved is normal expectoration.

10. The method of claim 2 wherein said dysfunction that is alleviated is chronic infection of the patient's respiratory tract.

11. The method of claim 2 wherein said dysfunction that is alleviated is inability to breathe normally after decannulation and said function that is improved is breathing after decannulation.

12. The method of claim 2 wherein said function that is improved is oxygenation of pulmonary blood.

13. The method of claim 2 wherein said function that is improved is ventilation of lower respiratory passages.

14. A tracheostomy valve unit adapted to cooperate with a tracheostomy tube inserted into a patient's trachea, said valve unit having:
    a first end adapted for connection to the free end of the tracheostomy tube and a second end
    a valve unit inlet located at the second end of said valve unit;
    conducting means for permitting airflow therethrough from said valve unit inlet through said valve unit and then to the tube to the patient's trachea, when the patient inhales; and
    blocking means making positive, uninterrupted closure contact with said valve unit inlet and thereby, entirely blocking airflow through said conducting means from the tube and through said valve unit inlet, at all times when the patient exhales and at all other times except when the patient inhales.

15. The apparatus of claim 14 wherein:
said valve unit having valve-seating means therein, located between said valve unit inlet and said blocking means;
said blocking means comprises a thin, flexible diaphragm and biasing means for biasing said diaphragm against said valve-seating means and thereby making positive, uninterrupted closure contact therewith.

16. The apparatus of claim 15 wherein said diaphragm is made of silicone sheet material.

17. The apparatus of claim 15 wherein said diaphragm is biased by said biasing means against said valve-seating means by a pressure of approximately 8 to 15 mm of water head.

18. The apparatus of claim 15 wherein:
   said valve unit includes anchoring means located within said valve unit inlet;
   said biasing means comprises rivet means for connecting said diaphragm to said anchoring means; and
   said rivet means is longitudinally compressed to a predetermined length to bias said diaphragm against said valve seating means.

19. The apparatus of claim 18 wherein the central portion of said diaphragm is displaced within said valve-seating means by said compressed rivet by approximately half the thickness of said diaphragm.

20. The apparatus of claim 18 wherein said diaphragm is approximately 0.6 inches in diameter, approximately 0.015 inches thick, and made of low-modulus silicone sheet material, and said diaphragm is preloaded against said valve seating means by displacing by said compressed rivet, means the central portion of said diaphragm within said above seating means by approximately 0.008 inches.

21. The apparatus of claim 15 wherein:
   said valve unit comprises a tubular structure which defines an air-transmission passage through said valve unit from end to end, said air transmission passage comprising said conducting means, and said tubular structure includes a transverse wall extending radially inwards at said second end and having at least one air port longitudinally extending therethrough, said at least one air port defining said valve unit inlet, said transverse wall having a tracheal face which is that face thereof adapted to face towards the trachea;
   said valve-seating means comprises an annular ring mounted to said tracheal face of said transverse wall, said ring adapted to extend toward the trachea away from said transverse wall and presenting a tracheal plane towards the trachea, and said ring having an inner edge located radially outwards from each said air port, so that each said port is wholly inside said ring;
   said valve unit further includes anchoring means located within said valve unit inlet;
   said biasing means comprises rivet means for connecting said diaphragm to said anchoring means;
   said rivet means presses said diaphragm against said tracheal plane of said ring, in said diaphragm's "rest" position, so that said diaphragm entirely obstructs each said air port, thereby entirely blocking airflow through said air-transmission passage; and
   said rivet means is longitudinally compressed to an extent that it presses a central portion of said diaphragm to a point axially intermediate between said tracheal face of said transverse wall and said tracheal plane of said ring.

22. The apparatus of claim 21 wherein said tubular structure has:
   a circular cross-section; and
   an internal taper at said first end such that said structure has a first inner diameter at said first end which is greater than a second inner diameter of said structure which is farther within said structure and more distant from said first end thereof, said first inner diameter being greater than the tracheostomy tube's outer diameter and said second inner diameter being less than the tracheostomy tube's outer diameter, whereby said valve unit slidably receives, and frictionally engages with, the free end of the tube and said valve unit is removably mounted on the tube.

23. The apparatus of claim 2 wherein said first inner diameter is approximately 15.5 mm and said second inner diameter is approximately 14.3 mm.

24. The apparatus of claim 15 wherein said valve unit inlet, includes means for fluidically connecting the valve unit to a respirator air outlet whereby said valve unit is inserted in-line between the respirator and the tracheostomy tube.

* * * * *